(12) United States Patent
Snell et al.

(10) Patent No.: US 10,232,360 B1
(45) Date of Patent: Mar. 19, 2019

(54) USE OF ORGANIC DOPANTS TO ENHANCE ACETYLENE HYDROGENATION CATALYSTS

(71) Applicant: Chevron Phillips Chemical Company LP, The Woodlands, TX (US)

(72) Inventors: Ryan W. Snell, Jubail Industrial (SA); Zongxuan Hong, Houston, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 15/702,411

(22) Filed: Sep. 12, 2017

(51) Int. Cl.
*B01J 23/44* (2006.01)
*B01J 21/04* (2006.01)
*B01J 21/06* (2006.01)
*B01J 31/02* (2006.01)
*C07C 7/167* (2006.01)
*B01J 31/28* (2006.01)
(Continued)

(52) U.S. Cl.
CPC .......... *B01J 31/0208* (2013.01); *B01J 31/28* (2013.01); *B01J 37/024* (2013.01); *B01J 37/16* (2013.01); *C07C 7/167* (2013.01); *B01J 2231/645* (2013.01)

(58) Field of Classification Search
CPC ...... B01J 31/0208; B01J 31/28; B01J 37/024; B01J 37/16; B01J 2231/645; C07C 7/167
USPC ................. 502/150, 330, 333, 339
See application file for complete search history.

(56) References Cited

U.S. PATENT DOCUMENTS 3,426,090 A * 2/1969 Fishel .................. B01J 21/04
585/269
3,576,865 A * 4/1971 Fleming et al. ....... A61K 31/16
544/357

(Continued)

OTHER PUBLICATIONS

Qin-Yu Zhu et al., "'Unsynnnnetric' palladium (II) complexes with ligand 4', 5'-diaza-9'-(4, 5-disubstituted-1,3-dithiole-2-ylidene)-fluorene." Inorganica Chimica Acta 351, pp. 177-182. (Year: 2003).*

(Continued)

*Primary Examiner* — Patricia L. Hailey
(74) *Attorney, Agent, or Firm* — Conley Rose, P.C.

(57) ABSTRACT

A composition comprising a supported hydrogenation catalyst comprising palladium and a support, wherein the supported hydrogenation catalyst is capable of selectively hydrogenating highly unsaturated hydrocarbons to unsaturated hydrocarbons; and a dopant comprising a fluorene structure. A method of making a selective hydrogenation catalyst including contacting a support with a palladium-containing compound to form a supported-palladium composition; contacting the supported-palladium composition with a dopant comprising a fluorene structure group to form a selective hydrogenation catalyst precursor; and reducing the selective hydrogenation catalyst precursor to form the selective hydrogenation catalyst. A method of selectively hydrogenating highly unsaturated hydrocarbons to an unsaturated hydrocarbon enriched composition by contacting a supported catalyst comprising palladium and a dopant comprising a fluorene structure with a feed comprising highly unsaturated hydrocarbon under conditions suitable for hydrogenating at least a portion of the highly unsaturated hydrocarbon feed to form the unsaturated hydrocarbon enriched composition.

28 Claims, 3 Drawing Sheets

(51) Int. Cl.
    *B01J 37/02*    (2006.01)
    *B01J 37/16*    (2006.01)

(56) References Cited

U.S. PATENT DOCUMENTS

| | | | |
|---|---|---|---|
| 3,644,486 A * | 2/1972 | Boldt et al. | C07C 67/055 |
| | | | 502/170 |
| 3,814,770 A * | 6/1974 | Andrews et al. | C07D 211/22 |
| | | | 546/203 |
| 4,404,124 A | 9/1983 | Johnson et al. | |
| 4,415,714 A | 11/1983 | Mack | |
| 4,484,015 A | 11/1984 | Johnson et al. | |
| 4,493,904 A | 1/1985 | Mack | |
| 6,319,428 B1 | 11/2001 | Michot et al. | |
| 9,181,356 B2 | 11/2015 | Hsieh et al. | |
| 9,346,719 B2 | 5/2016 | Shih et al. | |
| 2004/0037770 A1 * | 2/2004 | Fischer | B01J 23/42 |
| | | | 423/584 |
| 2004/0106798 A1 * | 6/2004 | Bremer | C07C 22/08 |
| | | | 544/294 |
| 2004/0241496 A1 * | 12/2004 | Zheng | C08G 61/02 |
| | | | 428/690 |
| 2006/0217579 A1 | 9/2006 | Bailey | |
| 2007/0114155 A1 | 5/2007 | Cholley et al. | |
| 2011/0065950 A1 | 3/2011 | Riisager et al. | |
| 2013/0102819 A1 | 4/2013 | Szesni et al. | |

OTHER PUBLICATIONS

Periodic Table of Elements, Feb. 4, 1985, C&EN, p. 27.

UOP Method 578-02, "Automated Pore Volume and Pore Size Distribution of Porous Substances by Mercury Porosimetry," UOP LLC, 1984, pp. 1-14.

Zhou et al., Ionic Liquid and Plasma Effects on SiO2 Supported Pd for Selective Hydrogenation of Acetylene. Catalysis Today, 2013, vol. 211, pp. 147-155, Elsevier B.V.

Filing receipt and specification for patent application entitled "Use of Charge-Containing Molecules Linked with Covalent Bonds to Enhance Acetylene Hydrogenation Catalysts," by Ryan W. Snell, et al., filed Sep. 12, 2017 U.S. Appl. No. 15/702,413.

Office Action dated Jun. 25, 2018 (13 pages), U.S. Appl. No. 15/702,413, filed Sep. 12, 2017.

Schobert, R., et al., "Compounds with Two Carton-Heteroatom Bonds. Heteroatom analogues of aldehydes and ketones," Science of Synthesis Category 4, 2004, Padwa Editor, Publishing Information & Table of Contents, pp. 973-974, vol. 27, Thieme.

* cited by examiner

US 10,232,360 B1

USE OF ORGANIC DOPANTS TO ENHANCE ACETYLENE HYDROGENATION CATALYSTS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Technical Field

The present disclosure relates to the production of unsaturated hydrocarbons, and more particularly to a selective hydrogenation catalyst and methods of making and using same.

Background

Unsaturated hydrocarbons such as ethylene and propylene are often employed as feedstocks in preparing value-added chemicals and polymers. Unsaturated hydrocarbons can be produced by pyrolysis or steam cracking of hydrocarbons including hydrocarbons derived from coal, hydrocarbons derived from synthetic crude, naphthas, refinery gases, ethane, propane, butane, and the like. Unsaturated hydrocarbons produced in these manners can contain small proportions of highly unsaturated hydrocarbons such as acetylenes and diolefins that can adversely affect the production of subsequent chemicals and polymers. Thus, to form an unsaturated hydrocarbon product, such as a polymer grade monoolefin, the amount of acetylenes and diolefins in the monoolefin stream is typically reduced. For example, in polymer grade ethylene, the acetylene content typically is less than about 2 ppmw.

One technique commonly used to reduce the amount of acetylenes and diolefins in an unsaturated hydrocarbon stream comprising primarily monoolefins involves selectively hydrogenating the acetylenes and diolefins to monoolefins. This process is selective in that hydrogenation of the monoolefin and the highly unsaturated hydrocarbons to saturated hydrocarbons is minimized. For example, the hydrogenation of ethylene or acetylene to ethane is minimized.

One challenge to the selective hydrogenation process is the potential for runaway reactions that lead to the uncontrollable reduction of unsaturated monoolefin (e.g., ethylene) to saturated hydrocarbon (e.g., ethane). One methodology to minimize runaway reactions is to increase the amount of selectivity enhancers in the hydrogenation catalyst. Thus, catalyst preparations may comprise one or more selectivity enhancers. Selectivity enhancers are materials, such as alkali metal halides, that increase the catalyst selectivity for the hydrogenation of highly unsaturated olefins to unsaturated olefins. The use of additional amounts of selectivity enhancers, also termed increased loadings, may lead to improved catalyst selectivity; however, the increased loadings may have drawbacks such as decreased catalyst activity.

One way to evaluate a selective hydrogenation catalyst is the operating window, which is the difference between two different determined temperature points, T1 and T2. T1 is the "clean-up" temperature, which can be defined to be the temperature at which a highly unsaturated hydrocarbon in the feed has been converted such that there is less than 20 ppmw in the product. T2 is the "runaway" temperature, where over hydrogenation has occurred to the point that ethane makes up 3 wt. % of the product. The larger the operating window, the more selective the catalyst is, and the less likely there is for unwanted runaway.

Therefore, a need exists for a selective hydrogenation catalyst that displays improved performance, such as an improved operating window and/or a desired selectivity and/or activity.

SUMMARY

Disclosed herein is a composition comprising a supported hydrogenation catalyst comprising palladium and a support, wherein the supported hydrogenation catalyst is capable of selectively hydrogenating highly unsaturated hydrocarbons to unsaturated hydrocarbons; and a dopant, wherein the dopant comprises a fluorene structure.

Also disclosed herein is a method of making a selective hydrogenation catalyst, the method comprising: contacting a support with a palladium-containing compound to form a supported-palladium composition; contacting the supported-palladium composition with a dopant to form a selective hydrogenation catalyst precursor, wherein the dopant comprises a fluorene structure group; and reducing the selective hydrogenation catalyst precursor to form the selective hydrogenation catalyst.

Also disclosed herein is a selective hydrogenation catalyst prepared according the herein-disclosed method of making a selective hydrogenation catalyst.

Also disclosed herein is a method of selectively hydrogenating highly unsaturated hydrocarbons to an unsaturated hydrocarbon enriched composition, the method comprising: contacting a supported catalyst comprising palladium and a dopant with a feed comprising highly unsaturated hydrocarbon under conditions suitable for hydrogenating at least a portion of the highly unsaturated hydrocarbon feed to form the unsaturated hydrocarbon enriched composition, wherein the dopant comprises a fluorene structure.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
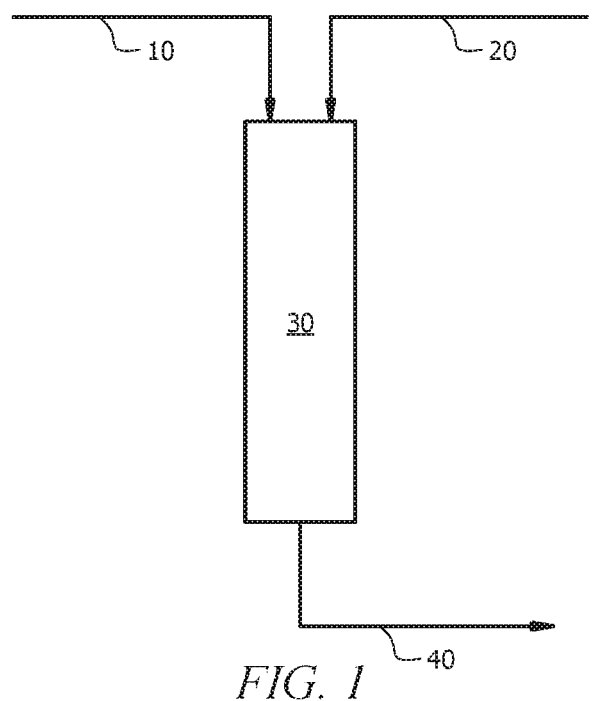
FIG. 1 is a process flow diagram of an embodiment of a selective hydrogenation process.

It should be understood at the outset that although an illustrative implementation of one or more embodiments is provided below, the disclosed systems and/or methods can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

In an embodiment, a method of making a selective hydrogenation catalyst comprises contacting an inorganic catalyst support with a palladium-containing compound to form a supported-palladium composition and contacting the supported-palladium composition with a dopant. Herein, the disclosure will focus on the use of dopants comprising organic molecules having a fluorene or fluorenone backbone, although other aromatic molecules may be suitable for use in this disclosure and will be described in more detail later herein. In an embodiment, the methodologies disclosed herein result in selective hydrogenation catalysts having enhanced selectivity, improved operating windows, and/or improved recovery from deactivation by sulfur. Catalysts of the type disclosed herein can be utilized as selective hydrogenation catalysts (SHC).

It is to be understood that the SHC is the result of contacting the components disclosed herein (e.g., inorganic support, palladium, dopant, etc.) to form a composition that can be utilized as a selective hydrogenation catalyst. The materials as utilized to form the SHC can contact and be converted such that the original material is not discernible as a separate entity in the SHC. For example, the disclosure will describe utilization of a metal-containing compound in the formation of the SHC. The SHC utilized as a selective hydrogenation catalyst can contain one or more components of the metal-containing compound; however, the metal-containing compound as originally contacted with the other components of the SHC may not be discernible in the final product.

The SHC can be used for selectively hydrogenating highly unsaturated hydrocarbons to unsaturated hydrocarbons. As used herein, a highly unsaturated hydrocarbon is defined as a hydrocarbon containing a triple bond, two conjugated carbon-carbon double bonds, or two cumulative carbon-carbon double bonds. As used herein, an unsaturated hydrocarbon is defined as a hydrocarbon containing an isolated carbon-carbon double bond. Examples of highly unsaturated hydrocarbons include, without limitation, acetylene, methylacetylene, and propadiene. Examples of unsaturated hydrocarbons include ethylene and propylene. It is also understood that the term "catalyst" refers to the support together with the materials impregnated in or on the support.

In an embodiment, the SHC can comprise an inorganic support such as, for example and without limitation, aluminas, silicas, titanias, zirconias, aluminosilicates (e.g., clays, ceramics, and/or zeolites), spinels (e.g., zinc aluminate, zinc titanate, and/or magnesium aluminate), or a combination thereof. In an embodiment, the SHC comprises an alumina support. In some embodiments, the alumina support comprises an alpha ($\alpha$)-alumina support.

The inorganic support can have a surface area of from about 2 to about 100 square meters per gram ($m^2/g$), alternatively of from about 2 $m^2/g$ to about 75 $m^2/g$, alternatively of from about 3 $m^2/g$ to about 50 $m^2/g$, alternatively of from about 4 $m^2/g$ to about 25 $m^2/g$, or alternatively of from about 5 $m^2/g$ to about 15 $m^2/g$. The surface area of the support can be determined using any suitable method. An example of a suitable method includes the Brunauer, Emmett, and Teller ("BET") method, which measures the quantity of nitrogen adsorbed on the support. Alternatively, the surface area of the support can be measured by a mercury intrusion method such as is described in ASTM UOP 578-02, entitled "Automated Pore Volume and Pore Size Distribution of Porous Substances by MERCURY Porosimetry," which is hereby incorporated herein by reference in its entirety for all purposes not contrary to this disclosure.

Particles of the inorganic support generally have an average diameter of from about 1 mm to about 10 mm, alternatively from about 2 mm to about 6 mm, alternatively from about 2 mm to about 4 mm, alternatively from about 3 mm to about 5 mm, alternatively from about 3.8 mm to about 4.2 mm, or alternatively from about 4 mm to about 6 mm, and can have any suitable shape. In an embodiment, the shape of the inorganic support can be cylindrical. In an alternative embodiment, the shape of the inorganic support can be spherical. In an embodiment, the inorganic support can be present in an amount such that it comprises the balance of the SHC when all other components are accounted for.

In an embodiment, the SHC comprises a Group 10 metal. Groups of elements of the table are indicated using the numbering scheme indicated in the version of the periodic table of elements published in *Chemical and Engineering News,* 63(5), 27, 1985. In an embodiment, the metals can comprise nickel, palladium, platinum, or combinations thereof. In an embodiment, the metal comprises palladium. Palladium can be added to the SHC by contacting the inorganic support with a palladium-containing compound to form a supported-palladium composition as will be described in more detail later herein. Examples of suitable palladium-containing compounds include, without limitation, palladium chloride, palladium nitrate, ammonium hexachloropalladate, ammonium tetrachloropalladate, palladium acetate, palladium bromide, palladium iodide, tetraamminepalladium nitrate, or combinations thereof. In an embodiment, the palladium-containing compound is a component of an aqueous solution. An example of a palladium-containing solution suitable for use in this disclosure includes, without limitation, a solution comprising palladium metal.

In an embodiment, the SHC can be prepared using a palladium-containing compound in an amount of from about 0.005 wt. % to about 5 wt. % based on the total weight of the SHC, alternatively from about 0.01 wt. % to about 3 wt. %, alternatively from about 0.02 wt. % to about 1 wt. %, alternatively from about 0.02 wt. % to about 0.04 wt. %, alternatively from about 0.018 wt. % to about 0.05 wt. %, or alternatively from about 0.03 wt. % to about 0.05 wt. %. The amount of palladium incorporated into the SHC can be in the range described herein for the amount of palladium-containing compound used to prepare the SHC.

In an embodiment, the SHC comprises a dopant. The dopant comprises an aromatic compound, and may be referred to herein as an 'aromatic dopant'. The aromatic dopant can comprise at least two benzene rings. In embodiments, the aromatic dopant comprises a fluorene structure or backbone as shown in structure (1):

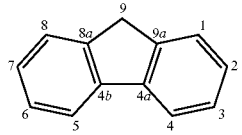

(1)

Such an aromatic dopant may also be referred to herein as a 'dopant comprising a fluorenyl group'. In embodiments, the aromatic dopant further comprises at least one substituent selected from carboxyl groups, hydroxyl groups, carbonyl groups, amide groups, hydrocarbyl groups, alcohol groups, halides, or combinations thereof. The terms "carboxyl group(s)," "hydroxyl group(s)," "carbonyl group(s)," "amide group(s)," "alcohol group(s)," and "halide(s)" are used herein in accordance with the definition specified by IUPAC. In embodiments, the substituent comprises a combination or substituted form of such groups, for example, a (hydroxymethyl)phenyl group. In embodiments, the at least one substituent is located on the 1 position, 2 position, 4 position, 9 position, or combinations thereof, of the fluorene structure, numbered as per structure (1) above.

For purposes of this application, the term "hydrocarbyl(s)" or "hydrocarbyl group(s)" are used herein in accordance with the definition specified by IUPAC: a univalent group or groups derived by the removal of one hydrogen atom from a carbon atom of a "hydrocarbon." A hydrocarbyl group can be an aliphatic, inclusive of acyclic and cyclic groups. A hydrocarbyl group can include rings, ring systems, aromatic rings, and aromatic ring systems. Hydrocarbyl groups can include, by way of example, aryl, alkyl, cycloalkyl, and combinations of these groups, among others. Hydrocarbyl groups can be linear or branched unless otherwise specified. For the purposes of this application, the terms "alkyl," or "cycloalkyl" refers to a univalent group derived by removal of a hydrogen atom from any carbon atom of an alkane. For example, in embodiments, the substituent comprises a methyl group. For the purposes of this application, the terms "aryl," or "arylene" refers to a univalent group derived by removal of a hydrogen atom from any carbon atom of an aryl ring. For example, in embodiments, the substituent comprises a phenyl group, a benzyl group, a substituted phenyl group, a substituted benzyl group, or a combination thereof.

In embodiments, the substituent comprises a carbonyl group in the 9 position of the fluorene structure, and the aromatic dopant has a fluorenone-type structure, comprising the fluorenone structure or backbone as shown in structure (2):

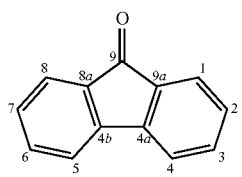

(2)

Upon reading this disclosure, one of skill in the art will recognize suitable aromatic dopants, and an exhaustive list of such will not be provided herein. By way of non-limiting examples, in embodiments, a fluorene-type dopant according to this disclosure may be selected from fluorene (i.e., 9H-fluorene), 9-phenyl-9-fluorenol, 9-hydroxyfluorene, 2-hydroxyfluorene, 9-(2-(hydroxymethyl)phenyl)-9-fluorenol, fluorene-9-carboxylic acid, fluorene-1-carboxylic acid, fluorene-4-carboxylic acid, fluorenone, or combinations thereof.

In embodiments, the aromatic dopant comprises multiple benzene rings separated by one or more groups not consisting of a cyclic ring structure. For example, in embodiments, the aromatic dopant is selected from ketones having the formula RC(=O)R', wherein both R and R' contain a phenyl group. By way of non-limiting example, such an aromatic dopant can comprise 1,3-diphenyl-1,3-propanedione, Michler's ketone (i.e., Bis[4-(dimethylamino)phenyl] methanone), chalcone (i.e., (2E)-1,3-Diphenylprop-2-en-1-one), or a combination thereof, or the like.

In embodiments, the aromatic dopant comprises no volatile heteroatoms. In embodiments, the aromatic dopant does not comprise phosphorus. In embodiments, the aromatic dopant comprises no elements other than carbon, hydrogen, oxygen, nitrogen, or halides. In embodiments, the aromatic dopant consists or consists essentially of carbon, hydrogen, oxygen, nitrogen, or halides. In embodiments, the aromatic dopant comprises only carbon, hydrogen, and/or oxygen. In embodiments, the aromatic dopant consists or consists essentially of only carbon, hydrogen, and/or oxygen. In embodiments, the aromatic dopant comprises a polynuclear aromatic.

An aromatic dopant suitable for use in this disclosure can be further characterized by a boiling point of greater than or equal to about 200° C., 250° C., or 300° C. at atmospheric pressure. In embodiments, the aromatic dopant is thermally stable and has a boiling point that is sufficiently high that the aromatic dopant doesn't desorb immediately from the catalyst surface during selective hydrogenation.

In an embodiment, the aromatic dopant can be present in the mixture for the preparation of the SHC in an amount of from about 0.005 wt. % to about 5 wt. % based on the weight of the dopant to the total weight of the SHC, alternatively from about 0.001 wt. % to about 5 wt. %, alternatively from about 0.001 wt. % to about 3 wt. %, or alternatively from about 0.005 wt. % to about 2 wt. %. In an embodiment, the aromatic dopant can be present in the mixture for the preparation of the SHC in an amount of less than or equal to about 5, 4, 3, 2, 1, or 0.5 wt. %. The amount of aromatic dopant incorporated into the SHC can be in the range described herein for the amount of dopant used to prepare the SHC.

In an embodiment, the SHC can further comprise one or more selectivity enhancers. Suitable selectivity enhancers include, but are not limited to, Group 1B metals, Group 1B metal compounds, silver compounds, gold compounds, fluorine, fluoride compounds, metals, alkali metal compounds, alkaline metals, alkaline metal compounds, iodine, iodide compounds, or combinations thereof. In an embodiment, the SHC comprises one or more selectivity enhancers which can be present in the mixture for preparation of the SHC in an amount of from about 0.001 wt. % to about 10 wt. % based on the total weight of the SHC, alternatively from about 0.01 wt. % to about 5 wt. %, alternatively from about 0.005 wt. % to about 5 wt. %, alternatively from about 0.01 wt. % to about 2 wt. %. The amount of selectivity enhancer incorporated into the SHC can be in the range described herein for the amount of selectivity enhancer used to prepare the SHC.

In an embodiment, the selectivity enhancer comprises silver (Ag), silver compounds, or combinations thereof. Examples of suitable silver compounds include, without limitation, silver nitrate, silver acetate, silver bromide, silver chloride, silver iodide, silver fluoride, or combinations thereof. In an embodiment, the selectivity enhancer comprises silver nitrate. The SHC can be prepared using silver nitrate in an amount of from about 0.005 wt. % to about 5 wt. % silver based on the total weight of the SHC, alternatively from about 0.01 wt. % to about 1 wt. % silver, alternatively from about 0.02 wt. % to about 0.5 wt. %, alternatively from about 0.03 wt. % to about 0.3 wt. %. The amount of silver incorporated into the SHC can be in the range described herein for the amount of silver nitrate used to prepare the SHC.

In an embodiment, the selectivity enhancer comprises alkali metals, alkali metal compounds, or combinations thereof. Examples of suitable alkali metal compounds include, without limitation, elemental alkali metal, alkali metal halides (e.g., alkali metal fluoride, alkali metal chloride, alkali metal bromide, alkali metal iodide), alkali metal oxides, alkali metal carbonate, alkali metal sulfate, alkali metal phosphate, alkali metal borate, or combinations thereof. In an embodiment, the selectivity enhancer comprises potassium fluoride (KF). In another embodiment, the SHC can be prepared using an alkali metal compound in an amount of from about 0.01 wt. % to about 5 wt. % based on the total weight of the SHC, alternatively from about 0.05 wt. % to about 2 wt. %, alternatively from about 0.05 wt. % to about 1 wt. %. The amount of alkali metal incorporated into the SHC can be in the range described herein for the amount of alkali metal compound used to prepare the SHC.

Although described hereinbelow with reference to a supported palladium composition and potassium fluoride and/or silver as optional selectivity enhancer(s) (e.g., supported Pd/KF, supported Pd/Ag, or supported Pd/KF/Ag), SHCs of this disclosure may be formed with any metal, support, and selectivity enhancer(s) described hereinabove, in combination with a dopant according to this disclosure.

In an embodiment, a method of preparing a SHC can initiate with the contacting of an inorganic support with a palladium-containing compound to form a supported-palladium composition. The contacting can be carried out using any suitable technique. For example, in embodiments, the inorganic support can be contacted with a solution of the palladium-containing compound by soaking in a volume of solution containing the palladium-containing compound that is greater than the pore volume of the support, i.e., by soaking with a greater volume of liquid than utilized during incipient wetness impregnation. In such embodiments, the resulting supported-palladium composition can have greater than about 90 wt. %, alternatively from about 92 wt. % to about 98 wt. %, alternatively from about 94 wt. % to about 96 wt. % of the palladium concentrated near the periphery of the supported-palladium composition, as to form a palladium skin.

The palladium skin can be any thickness as long as such skin thickness can promote the hydrogenation processes disclosed herein. Generally, the thickness of the palladium skin can be in the range of from about 1 micron to about 3000 microns, alternatively from about 5 microns to about 2000 microns, alternatively from about 10 microns to about 1000 microns, alternatively from about 50 microns to about 500 microns. Examples of such methods are further described in more details in U.S. Pat. Nos. 4,404,124 and 4,484,015, each of which is hereby incorporated herein by reference in its entirety for all purposes not contrary to this disclosure.

Any suitable method can be used for determining the thickness of the palladium skin of the supported-palladium composition, selective hydrogenation catalyst and/or SHC composition. For example, one method involves breaking open a representative sample of the SHC and treating the catalyst pieces with a dilute alcoholic solution of N,N-dimethyl-para-nitrosoaniline. The treating solution can react with the palladium to give a red color that can be used to evaluate the distribution of the palladium on the catalyst. Yet another technique for measuring the concentration of the palladium in the skin of the SHC involves breaking open a representative sample of catalyst, followed by treating the catalyst pieces with a reducing agent such as hydrogen to change the color of the skin and thereby evaluate the distribution of the palladium. Alternatively, the palladium skin thickness can be determined by analyzing a cross-section of the catalyst using an electron microprobe analyzer.

The supported-palladium composition formed by contacting the inorganic support with a solution of a palladium-containing compound can optionally be dried at a temperature of from about 15° C. to about 150° C., alternatively from about 30° C. to about 100° C., or alternatively from about 60° C. to about 100° C.; and for a period of from about 0.1 hour to about 100 hours, alternatively from about 0.5 hour to about 20 hours, or alternatively from about 1 hour to about 10 hours. Alternatively or additionally, the supported-palladium composition can be calcined. This calcining step can be carried out at temperatures up to about 850° C., alternatively of from about 150° C. to about 700° C., alternatively from about 150° C. to about 600° C., or alternatively from about 150° C. to about 550° C.; and for a period of from about 0.2 hour to about 20 hours, alternatively from about 0.5 hour to about 20 hours, or alternatively from about 1 hour to about 10 hours. In an embodiment, the supported-palladium composition can be dried and subsequently calcined.

In an embodiment, a method of preparing a SHC further comprises contacting the supported-palladium composition with an aromatic dopant of the type described herein (e.g., a fluorene or fluorenone-type compound or a composition, e.g., solution, comprising same).

In an embodiment, the aromatic dopant is contacted with the supported-palladium composition. The contacting can be carried out in any suitable manner that will yield a selective hydrogenation catalyst meeting the parameters described herein; such as for example by incipient wetness impregnation. Herein a SHC is formed by the contacting of a supported-palladium composition with an aromatic dopant is designated as a Pd/D. Briefly, the aromatic dopant can be dissolved in a solvent to form a dopant-containing solution. The solvent can be any suitable solvent in which the aromatic dopant dissolves. In embodiments, the solvent can be readily removed via drying and calcining (i.e., the solvent has a reasonably high volatility) as well as have a low level of toxicity. In an embodiment, the solvent comprises an organic solvent selected from toluene, benzene, acetone, dimethyl sulfoxide (DMSO), carbon tetrachloride, and the like. Desirably, the solvent is an organic alcohol, such as butanol or ethanol. The aromatic dopant may be combined with the solvent such that the aromatic dopant is present in the solvent in an amount of from about 0.1 wt. % to about 15 wt. %, from about 0.5 wt. % to about 10 wt. %, or from about 1 wt. % to about 8 wt. %. In an embodiment, the supported-palladium composition can be added to or combined with the aromatic dopant solution to form the Pd/D composition.

In an embodiment, silver can be added to the supported-palladium composition (without a dopant). For example, the supported-palladium composition can be placed in an aqueous silver nitrate solution of a quantity greater than that necessary to fill the pore volume of the composition. The resulting material can be a supported palladium/silver composition (herein this particular embodiment is referred to as a Pd/Ag composition).

In an embodiment, the Pd/Ag composition is further contacted with an aromatic dopant. The contacting can be carried out as described above, to form a Pd/Ag/D.

In an embodiment, one or more alkali metals can be added to the Pd/Ag composition (prior to or following contacting with an aromatic dopant) using any suitable technique such as those described previously herein. In an embodiment, the selectivity enhancer comprises an alkali fluoride, and the resulting material is a palladium/silver/alkali metal fluoride supported composition. In an embodiment, the selectivity enhancer comprises potassium fluoride, and the resulting material is a palladium/silver/potassium fluoride (Pd/Ag/KF) supported composition.

In an embodiment, the supported-palladium composition is contacted with both an alkali metal halide and a silver compound (prior to or following contacting with an aromatic dopant). Contacting of the supported-palladium composition with both an alkali metal halide and a silver compound can be carried out simultaneously; alternatively, the contacting can be carried out sequentially in any user-desired order.

In an embodiment, one or more selectivity enhancers can be contacted with the supported-palladium composition prior to contacting the composition with a dopant. In such embodiments, the resulting composition (e.g., comprising Pd/Ag, Pd/KF, or Pd/Ag/KF) can be calcined under the conditions described previously herein and subsequently contacted with an aromatic dopant. For example, an aromatic dopant can be added to the Pd/Ag, Pd/KF, and/or Pd/Ag/KF composition to provide Pd/Ag/D, Pd/KF/D, and/or Pd/Ag/KF/D compositions, respectively. In an alternative embodiment, one or more selectivity enhancers can be contacted with the supported-palladium composition following contacting of the composition with an aromatic dopant. For example, Ag and/or KF can be added to the Pd/D composition to provide Pd/Ag/D, Pd/KF/D, and/or Pd/Ag/KF/D compositions. In yet another alternative embodiment, one or more selectivity enhancers can be contacted with the supported-palladium composition and aromatic dopant simultaneously.

In an embodiment, a method of preparing a SHC of the type disclosed herein comprises contacting an α-alumina support, palladium, and an aromatic dopant, each of the type previously disclosed herein. In an alternative embodiment, a method of preparing a SHC of the type disclosed herein comprises contacting an α-alumina support, palladium, an aromatic dopant, and one or more selectivity enhancers, (e.g., silver and/or potassium fluoride). The resultant materials (Pd/D, Pd/Ag/D, Pd/KF/D, and/or Pd/Ag/KF/D compositions) can be dried to form a dried catalyst composition. In some embodiments, this drying step can be carried out at a temperature in the range of from about 0° C. to about 150° C., alternatively from about 30° C. to about 100° C., alternatively from about 50° C. to about 80° C.; and for a period of from about 0.1 hour to about 100 hours, alternatively from about 0.5 hour to about 20 hours, or alternatively from about 1 hour to about 10 hours at pressures ranging from ambient to 100 torr of vacuum. In an embodiment, an aromatic dopant precursor is employed so that upon exposure to air and/or the temperature ranges used during drying of the aforementioned composition it is converted to an aromatic dopant of the type described. For example, some fluorene could be oxidized to fluorenone during the drying step. In some embodiments, this drying step can be carried out at ambient pressure, alternatively, this drying step can be carried out at a pressure from about 0.1 atm to 1 atm.

The dried catalyst composition can be reduced using hydrogen gas or a hydrogen gas containing feed, e.g., the feed stream of the selective hydrogenation process, thereby providing for optimum operation of the selective hydrogenation process to form a SHC. Such a gaseous hydrogen reduction can be carried out at a temperature in the range of from, for example, about 0° C. to about 150° C., alternatively about 20° C. to about 100° C., or alternatively about 25° C. to about 80° C.

In an embodiment, a method of preparing a SHC comprises contacting an inorganic support with a palladium-containing compound (e.g., palladium chloride, palladium nitrate) to form a supported-palladium composition and drying and calcining the supported-palladium composition to form a dried and calcined supported-palladium composition. The dried and calcined supported-palladium composition can then be contacted with a silver-containing compound (e.g., silver nitrite, silver fluoride) to form a Pd/Ag composition, which can then be dried and/or calcined to form a dried and/or calcined Pd/Ag composition. The dried and/or calcined Pd/Ag composition can be contacted with an alkali metal fluoride (e.g., potassium fluoride) to form a Pd/Ag/KF composition that is then dried and calcined. The dried and calcined Pd/Ag/KF composition can then be contacted with an aromatic dopant to form a catalyst composition that is subsequently reduced to form a SHC.

In some embodiments, the SHC can be formed from a palladium/silver/alkali metal salt composition that has been contacted with an aromatic dopant. In some embodiments, the resultant material is a catalyst precursor that can be further treated to form a SHC. In some embodiments, further treatments comprise drying. In some embodiments, further treatments comprise reducing. In some embodiments, further treatments comprise drying and reducing.

In an embodiment, the SHC catalyzes a selective hydrogenation process. In such processes, the SHC can be contacted with an unsaturated hydrocarbon stream primarily containing unsaturated hydrocarbons, e.g., ethylene, but also containing a highly unsaturated hydrocarbon, e.g., acetylene. The contacting can be executed in the presence of hydrogen at conditions effective to selectively hydrogenate the highly unsaturated hydrocarbon to an unsaturated hydrocarbon. In an embodiment, SHCs of the type disclosed herein are used in the hydrogenation of highly unsaturated hydrocarbons such as, for example and without limitation, acetylene, methylacetylene, propadiene, butadiene or combinations thereof.

FIG. 1 illustrates an embodiment of a hydrogenation process that utilizes a SHC of the type disclosed herein. The hydrogenation process includes feeding an unsaturated hydrocarbon stream 10 and a hydrogen ($H_2$) stream 20 to a hydrogenation reactor 30 within which the SHC is disposed. The unsaturated hydrocarbon stream 10 primarily comprises one or more unsaturated hydrocarbons, but it can also contain one or more highly unsaturated hydrocarbons such as, for example and without limitation, acetylene, methylacetylene, propadiene, and butadiene. Alternatively, unsaturated hydrocarbon stream 10 and hydrogen stream 20 can be combined in a single stream that is fed to hydrogenation reactor 30.

In an embodiment, reactor 30 is a selective hydrogenation reactor that can belong to an acetylene removal unit of an unsaturated hydrocarbon production plant in a backend configuration. As used herein, "backend" refers to the location of the acetylene removal unit in an unsaturated hydrocarbon production unit that receives a lower boiling fraction from a deethanizer fractionation tower. The deethanizer tower receives a higher boiling fraction from a demethanizer fractionation tower. The demethanizer tower receives a feed from an unsaturated hydrocarbon production process.

In an embodiment, reactor 30 is a selective hydrogenation reactor that can belong to an acetylene removal unit of an unsaturated hydrocarbon production plant in a frontend deethanizer configuration. As used herein, "frontend deethanizer" refers to the location of the acetylene removal unit in an unsaturated hydrocarbon production unit that receives a lower boiling fraction from a deethanizer fractionation tower. The deethanizer tower receives a feed from an unsaturated hydrocarbon production process.

In an embodiment, reactor 30 is a selective hydrogenation reactor that can belong to an acetylene removal unit of an unsaturated hydrocarbon production plant in a frontend depropanizer configuration. As used herein, "frontend depropanizer" refers to the location of the acetylene removal unit in an unsaturated hydrocarbon production unit that receives a lower boiling fraction from a depropanizer fractionation. The depropanizer tower a feed from an unsaturated hydrocarbon production process.

In an embodiment, reactor 30 is a selective hydrogenation reactor that can belong to an acetylene removal unit of an unsaturated hydrocarbon production plant in a raw gas configuration. As used herein, "raw gas" refers to the location of the acetylene removal unit in an unsaturated hydrocarbon production unit that receives a feed from an unsaturated hydrocarbon production process without any intervening hydrocarbon fractionation.

It is understood that hydrogenation reactor 30, and likewise the selective hydrogenation catalysts disclosed herein, are not limited to use in backend acetylene removal units, frontend deethanizer units, frontend depropanizer, or raw gas units and can be used in any process wherein a highly unsaturated hydrocarbon contained within an unsaturated hydrocarbon stream is selectively hydrogenated to a unsaturated hydrocarbon.

In embodiments wherein the acetylene removal unit is in a backend configuration, the highly unsaturated hydrocarbon being fed to hydrogenation reactor 30 comprises acetylene. The mole ratio of the hydrogen to the acetylene being fed to hydrogenation reactor 30 can be in the range of from about 0.1 to about 10, alternatively from about 0.2 to about 5, alternatively from about 0.5 to about 3.

In embodiments wherein the acetylene removal unit is in a front-end deethanizer, front-end depropanizer or raw gas configuration, the highly unsaturated hydrocarbon being fed to hydrogenation reactor 30 comprises acetylene. In such an embodiment, the mole ratio of the hydrogen to the acetylene being fed to hydrogenation reactor 30 can be in the range of from about 10 to about 3000, alternatively from about 10 to about 2000, alternatively from about 10 to about 1500.

In embodiments wherein the acetylene removal unit is in a front-end depropanizer or raw gas configuration, the highly unsaturated hydrocarbon being fed to hydrogenation reactor 30 comprises methylacetylene. In such an embodiment, the mole ratio of the hydrogen to the methylacetylene being fed to hydrogenation reactor 30 can be in the range of from about 3 to about 3000, alternatively from about 5 to about 2000, alternatively from about 10 to about 1500.

In embodiments wherein the acetylene removal unit is in a front-end depropanizer or raw gas configuration, the highly unsaturated hydrocarbon being fed to hydrogenation reactor 30 comprises propadiene. In such an embodiment, the mole ratio of the hydrogen to the propadiene being fed to hydrogenation reactor 30 can be in the range of from about 3 to about 3000, alternatively from about 5 to about 2000, alternatively from about 10 to about 1500.

In another embodiment, reactor 30 can represent a plurality of reactors. The plurality of reactors can optionally be separated by a means to remove heat produced by the reaction. The plurality of reactors can optionally be separated by a means to control inlet and effluent flows from reactors or heat removal means allowing for individual, or alternatively, groups of reactors within the plurality of reactors to be regenerated. The selective hydrogenation catalyst can be arranged in any suitable configuration within hydrogenation reactor 30, such as a fixed catalyst bed.

Carbon monoxide can also be fed to reactor 30 via a separate stream (not shown), or it can be combined with hydrogen stream 20. In an embodiment, the amount of carbon monoxide being fed to reactor 30 during the hydrogenation process is less than about 0.15 mol % based on the total moles of fluid being fed to reactor 30.

Hydrogenation reactor 30 can be operated at conditions effective for selective hydrogenation of the highly unsaturated hydrocarbons to one or more unsaturated hydrocarbons upon contacting the selective hydrogenation catalyst in the presence of the hydrogen. The conditions are desirably effective to maximize hydrogenation of highly unsaturated hydrocarbons to unsaturated hydrocarbons and to minimize hydrogenation of highly unsaturated hydrocarbons and unsaturated hydrocarbons to saturated hydrocarbons. In some embodiments, acetylene can be selectively hydrogenated to ethylene. Alternatively, methylacetylene can be selectively hydrogenated to propylene. Alternatively, propadiene can be selectively hydrogenated to propylene. Alternatively, butadiene can be selectively hydrogenated to butenes. In some embodiments, the temperature within the hydrogenation zone can be in the range of from about 5° C. to about 300° C., alternatively from about 10° C. to about 250° C., alternatively from about 15° C. to about 200° C. In some embodiments, the pressure within the hydrogenation zone can be in the range of from about 15 (204 kPa) to about 2,000 (13,890 kPa) pounds per square inch gauge (psig), alternatively from about 50 psig (446 kPa) to about 1,500 psig (10,443 kPa), alternatively from about 100 psig (790 kPa) to about 1,000 psig (6,996 kPa).

Referring back to FIG. 1, an effluent stream 40 comprising unsaturated hydrocarbons, including the one or more monoolefins produced in hydrogenation reactor 30, and any unconverted reactants exit hydrogenation reactor 30. In an embodiment, effluent stream 40 primarily comprises ethylene and/or comprises less than about 5 ppmw, alternatively less than about 1 ppmw of highly unsaturated hydrocarbons.

In an embodiment, a SHC of the type described herein can have a comparable catalytic activity when compared to an otherwise similar selective hydrogenation catalyst prepared in the absence of an aromatic dopant (e.g., compared to an SHC comprising Pd/Ag, Pd/KF, or Pd/Ag/KF). The comparable catalytic activity can translate to a comparable clean up temperature. Herein, the clean-up temperature is designated T1 and refers to the temperature at which the concentration of highly unsaturated hydrocarbon (e.g., acetylene) concentration drops below 20 ppmw in a feed stream comprising unsaturated hydrocarbon and highly unsaturated hydrocarbons such as acetylene and diolefins. In an embodiment, a SHC of the type disclosed herein can have a T1 of from about 90° F. to about 130° F., alternatively from about 95° F. to about 120° F., alternatively from about 100° F. to about 115° F.

In an embodiment, a SHC can exhibit an increased selectivity when compared to an otherwise similar SHC prepared in the absence of an aromatic dopant (e.g., compared to an SHC comprising Pd/Ag, Pd/KF, or Pd/Ag/KF). Herein selectivity refers to a comparison between the rate at which the SHC converts a highly unsaturated hydrocarbon to an unsaturated hydrocarbon, herein termed Conversion 1, and the rate at which the SHC converts an unsaturated hydrocarbon to a saturated hydrocarbon, herein termed Conversion 2. A SHC can display an increased rate of Conversion 1 and a decreased rate of Conversion 2 when compared to an otherwise similar catalyst prepared in the absence of an aromatic dopant of the type described herein (e.g., compared to an SHC comprising Pd/Ag, Pd/KF, or Pd/Ag/KF). Conversion 2 is highly exothermic and can lead to runaway reactions or the uncontrollable conversion of unsaturated hydrocarbons to saturated hydrocarbons due to the presence of excess unsaturated hydrocarbons. The higher selectivity of the SHC can, in embodiments, result in a reduction in the incidence of runaway reactions and increase the operating window of the hydrogenation process.

In embodiments, the highly unsaturated hydrocarbons comprise acetylene, and the operating window is at least about 10° F., 15° F., 20° F., 25° F., 30° F. or 35° F. greater than a method utilizing an otherwise similar composition prepared with a catalyst lacking the aromatic dopant (e.g., compared to an SHC comprising Pd/Ag, Pd/KF, or Pd/Ag/KF).

An operating window ($\Delta T$) is defined as the difference between a runaway temperature ($T2$) at which 3 wt. % of saturated hydrocarbon (e.g., ethane) is found in the product of a reaction having a feedstock comprising highly unsaturated and unsaturated hydrocarbons, and the clean-up temperature ($T1$). $\Delta T$ is a convenient measure of the operational stability of a selective hydrogenation catalyst for the hydrogenation of highly unsaturated hydrocarbons (e.g., acetylene) to unsaturated hydrocarbons (e.g., ethylene). The more stable a hydrogenation catalyst, the higher the temperature beyond $T1$ required to hydrogenate a given unsaturated hydrocarbon (e.g., ethylene). The $T2$ is coincident with the temperature at which a high probability exists for a runaway ethylene hydrogenation reaction to occur in an adiabatic reactor. Therefore, a larger $\Delta T$ translates to a more stable catalyst and a wider operation window for the complete acetylene hydrogenation.

In an embodiment, a SHC of the type disclosed herein can have an operating window of from about 25° F. to about 140° F., alternatively from about 40° F. to about 130° F., or alternatively from about 50° F. to about 120° F. In an embodiment, a SHC of the type disclosed herein can have an operating window of greater than or equal to about 60° F., 70° F., or 80° F. The operating window of a SHC of the type described herein can be increased by greater than about 70%, alternatively greater than about 80%, alternatively greater than about 90%, or alternatively greater than about 100% when compared to an otherwise similar catalyst prepared in the absence of an aromatic dopant (e.g., compared to an SHC comprising Pd/Ag, Pd/KF, or Pd/Ag/KF). A higher operating window indicates a more selective SHC. Selectivity typically refers to the percent ethylene conversion of acetylene at $T1$.

In embodiments, a SHC of this disclosure is desirable from an environmental health and safety standpoint. For example, an aromatic dopant as described herein may be less volatile than other dopants known in the art. Utilization of a thermally stable aromatic dopant as described herein, may reduce concerns of a volatile dopant remaining in the unsaturated hydrocarbon (e.g., ethylene) product. In embodiments, an aromatic dopant as provided herein has a low toxicity. Such a low toxicity may be indicated by an NFPA 704 Health Rating of less than or equal to 2, 1, or 0.

In an embodiment, a SHC can display activity comparable to or greater than an otherwise similar SHC prepared in the absence of an aromatic dopant (e.g., compared to an SHC comprising Pd/Ag, Pd/KF, or Pd/Ag/KF). In an embodiment, a SHC can display a more constant activity relative to an otherwise similar SHC prepared in the absence of an aromatic dopant (e.g., compared to an SHC comprising Pd/Ag, Pd/KF, or Pd/Ag/KF). In an embodiment, a SHC comprising a supported-palladium catalyst composition with an aromatic dopant of the type described (e.g., Pd/D) herein can result in the catalyst displaying a selectivity and activity comparable to that of a hydrogenation catalyst comprising one or more selectivity enhancers (e.g., compared to Pd/Ag, Pd/KF, or Pd/Ag/KF). In another embodiment, treatment of a hydrogenation catalyst comprising a single selectivity enhancer with an aromatic dopant of the type described herein (e.g., Pd/Ag/D or Pd/KF/D) can result in the catalyst displaying a selectivity and activity comparable to that of a hydrogenation catalyst comprising at least two selectivity enhancers (e.g., Pd/Ag/KF).

A method for the selective hydrogenation of a hydrocarbon feed comprising highly unsaturated and unsaturated hydrocarbons can comprise the preparation of a SHC catalyst comprising an aromatic dopant of the type disclosed herein having a boiling point below a maximum temperature attained during selective hydrogenation and contacting of the SHC with the hydrocarbon feed in a reactor having an initial temperature ($T0$). The aromatic dopant can remain associated with the SHC upon start of the reaction at $T0$. Depending on the boiling point of the aromatic dopant, over time if the temperature increases above the boiling point of the aromatic dopant, the aromatic dopant can be evaporated (i.e., boiled off) from the SHC. The SHC prepared utilizing the aromatic dopant can display an increased activity over time and an enhanced initial selectivity when the aromatic dopant is associated or has been associated with the SHC. This can be advantageous for reactions employing a fresh catalyst as a SHC prepared utilizing the aromatic dopant can allow for a more stable operation and a reduction in the potential for a runaway reaction due to the increase in catalyst selectivity and predictable catalytic activity as the composition stabilizes. In other words, the presence of the SHC prepared utilizing the aromatic dopant can aid in the control of the reaction during start up following a catalyst change out. Following the loss of the aromatic dopant, the resulting composition can display an activity and selectivity comparable to that of an otherwise similar catalyst prepared in the absence of an aromatic dopant (e.g., an SHC comprising Pd/Ag, Pd/KF, or Pd/Ag/KF).

In an alternative embodiment, a method for the selective hydrogenation of a hydrocarbon feed comprising highly unsaturated and unsaturated hydrocarbons comprises the preparation of a SHC comprising a high boiling point aromatic dopant (i.e., having a boiling point above a maximum temperature attained during selective hydrogenation), as described previously herein, and contacting of the SHC with the hydrocarbon feed. The high boiling point aromatic dopant compound can remain associated with the SHC throughout the lifetime of the catalyst providing the reaction temperature remains below the boiling point of the high boiling point aromatic dopant. The SHC prepared utilizing the high boiling point aromatic dopant can display improvements in characteristics such as catalytic activity and selectivity when compared to an otherwise similar catalyst composition prepared in the absence of an aromatic dopant (e.g., compared to an SHC comprising Pd/Ag, Pd/KF, or Pd/Ag/KF).

In an alternative embodiment, a method for the selective hydrogenation of a hydrocarbon feed comprising highly unsaturated and unsaturated hydrocarbons comprises the preparation of a SHC comprising a high boiling point aromatic dopant and a low boiling point aromatic dopant, each of the type described previously herein, and contacting of the SHC with the hydrocarbon feed. The SHC prepared utilizing both the low boiling point aromatic dopant, and the high boiling point aromatic dopant can display improvements in characteristics such as catalytic activity and selectivity when compared to an otherwise similar catalyst composition prepared in the absence of an aromatic dopant (e.g., compared to an SHC comprising Pd/Ag, Pd/KF, or Pd/Ag/KF). Further, these SHCs comprising one or more aromatic dopants can be advantageous for reactions employing a fresh catalyst, as such SHCs can allow for a more stable operation and a reduction in the potential for runaway reactions due to the increase in catalyst selectivity and predictable catalytic activity as the composition stabilizes.

EXAMPLES

The disclosure having been generally described, the following examples are given as particular embodiments of the disclosure and to demonstrate the practice and advantages thereof. It is understood that the examples are given by way of illustration and are not intended to limit the specification or the claims to follow in any manner.

Example 1: Comparison of Pd/Ag/KF and Pd/Ag/KF/D Catalysts

To study the effect of an SHC according to this disclosure, a Pd/Ag/KF/D catalyst according to this disclosure comprising 1 weight percent fluorenone as dopant was studied.

A comparative or 'baseline' Pd/Ag/KF catalyst, CC1, was prepared using a commercial Pd/Ag/KF catalyst/alpha-$Al_2O_3$ pellets, supplied by Süd Chemie of Huefeld, Germany, in the form of 4 mm×4 mm tablets as described in U.S. Pat. No. 4,484,015, which is hereby incorporated herein by reference in its entirety for all purposes not contrary to this disclosure. The alpha-$Al_2O_3$ pellets had a surface area of about 5 to about 7 $m_2/g$ (determined by the BET method employing N2 adsorption).

More specifically, 100 g of alumina support was impregnated with a solution of 100 g $PdCl_2$ solution with Pd concentration at 400 ppmw. This catalyst was then dried at 90° C. for 1 hour, at 200° C. for 1 hour, at 400° C. for 1 hour, and at 540° C. for 3 hours, resulting in a catalyst comprising 400 ppm by weight (ppmw) palladium. The above Pd/alpha-$Al_2O_3$ pellets were then impregnated with a solution of 100 g $AgNO_3$ solution having a Ag concentration at 410 ppmw. This catalyst was then dried at 90° C. for 1 hour, at 200° C. for 1 hour, at 400° C. for 1 hour, and at 540° C. for 3 hours, resulting in a catalyst comprising 400 ppm by weight (ppmw) palladium and 400 ppm by weight (ppmw) silver. The above catalyst was further impregnated by incipient wetness with a KF solution comprising 0.149 g of KF dissolved in 26 g of water. This catalyst was then dried at 90° C. for 1 hour, at 200° C. for 1 hour, at 400° C. for 1 hour, and at 540° C. for 3 hours, resulting in a catalyst comprising 400 ppm by weight (ppmw) palladium, 400 ppm by weight (ppmw) silver, and 1000 ppmw potassium.

A Pd/Ag/KF/D SHC according to this disclosure, SHC-1, was prepared by dissolving 1 g of fluorenone into 40 mL of toluene, and impregnating 100 g of the CC1 catalyst composition with the fluorenone containing solution. The impregnated catalyst was then allowed to sit open in a hood overnight to dry.

Twenty (20) mL of catalyst was then loaded into a reactor and reduced for 60 minutes at 100° F. in 200 mL/min $H_2$ and 200 psig. The catalyst was then used to hydrogenate an acetylene-containing gas mixture. The synthetic feed used in these examples is typical of a feed from the top of a deethanizer fractionation tower in an ethylene plant, with the exception that ethane was replaced with methane in the synthetic feed so that any ethane found in the reactor effluent was the result of the hydrogenation of ethylene. The synthetic feed contained approximately 25.8 mole percent methane, 47.4 mole percent ethylene, 0.16 mole percent acetylene, 26.6 mole percent hydrogen, and 0.034 mole percent carbon monoxide.

Figure 2:
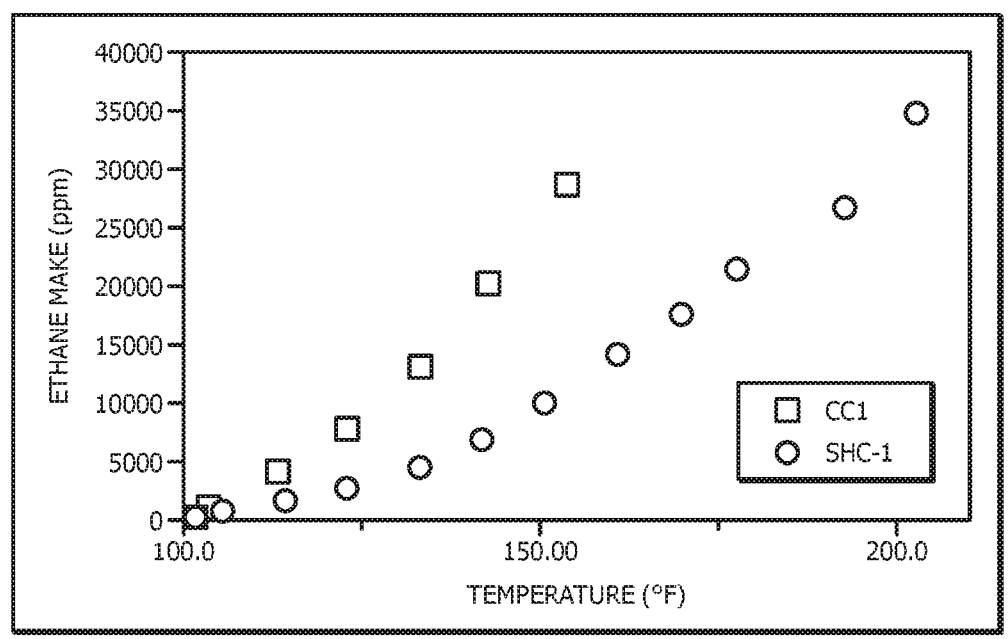
FIG. 2 is a plot of ethane make as a function of temperature for the catalysts of Example 1.

Results of this fluorenone containing catalyst along with the baseline CC1 catalyst are shown below in FIG. 2 and Table 1. FIG. 2 is a plot of ethane make (ppm) as a function of temperature (° F.) for the CC1 and SHC-1 catalysts. The fluorenone containing SHC-1 catalyst is superior to the comparative CC1 catalyst with respect to selectivity and operating window, having an operating window 73% greater than the comparative catalyst. Additionally, the starting activity of SHC-1 (as indicated by T1) is comparable to that of the CC1 catalyst.

TABLE 1

| Pd/Ag/KF and Pd/Ag/KF/D Catalyst Performance from Example 1 | | |
|---|---|---|
| | CC1 | SHC-1 |
| T1 (° F.) | 103 | 105 |
| T2 (° F.) | 159 | 202 |
| Operating Window (° F.) | 56 | 97 |

Example 2: Comparison of Pd/KF (1000 ppm) and Pd/KF (1000 ppm)/D Catalysts

To further study the effect of an SHC according to this disclosure, a Pd/KF/D catalyst according to this disclosure comprising 1 weight percent fluorenone as dopant was studied. A comparative Pd/KF catalyst, CC2, was prepared by adding KF by incipient wetness onto a Pd/alumina catalyst, resulting in a catalyst comprising 400 ppm by weight (ppmw) palladium, and 1000 ppmw potassium.

A Pd/KF/D SHC according to this disclosure, SHC-2, was prepared by dissolving 1 g of fluorenone into 40 mL of toluene, and impregnating 100 g of the CC2 catalyst composition with the fluorenone containing solution. The impregnated catalyst was then allowed to sit open in a hood overnight to dry. The catalysts were reduced and utilized to hydrogenate an acetylene-containing gas mixture, as described in Example 1.

Figure 3:
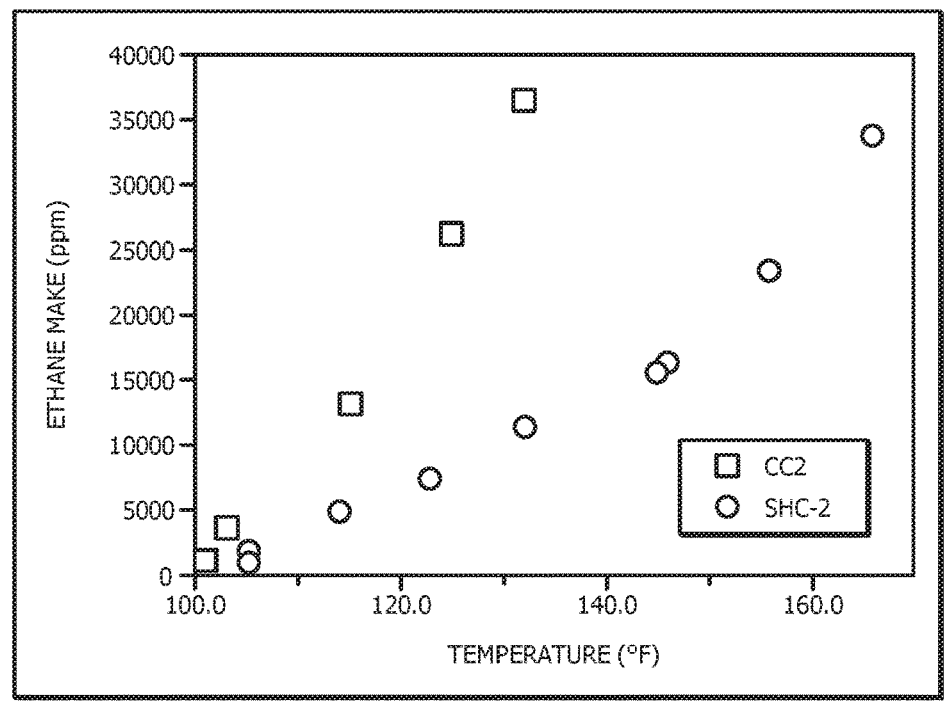
FIG. 3 is a plot of ethane make as a function of temperature for the catalysts of Example 2.

Results of this fluorenone containing catalyst along with the baseline CC2 catalyst are shown below in FIG. 3 and Table 2. FIG. 3 is a plot of ethane make (ppm) as a function of temperature (° F.) for the CC2 and SHC-2 catalysts. The fluorenone containing SHC-2 catalyst is superior to the comparative CC2 catalyst with respect to selectivity and operating window, having an operating window 113% greater than the comparative catalyst. Additionally, the starting activity of SHC-2 (as indicated by T1) is comparable to that of the CC2 catalyst.

TABLE 2

Pd/KF and Pd/KF/D Catalyst Performance from Example 2

|  | CC2 | SHC-2 |
|---|---|---|
| T1 (° F.) | 102 | 104 |
| T2 (° F.) | 131 | 166 |
| Operating Window (° F.) | 29 | 62 |

Example 3: Comparison of Pd/KF (3000 ppm) and Pd/KF (3000 ppm)/D Catalysts

To further study the effect of an SHC according to this disclosure, a Pd/KF (3000 ppm)/D catalyst according to this disclosure comprising 1 weight percent fluorenone as dopant was studied. A comparative Pd/KF catalyst, CC3, was prepared by adding KF by incipient wetness onto a Pd/alumina catalyst, resulting in a catalyst comprising 400 ppm by weight (ppmw) palladium, and 3000 ppmw potassium.

A Pd/KF (3000 ppm)/D SHC according to this disclosure, SHC-3, was prepared by dissolving 1 g of fluorenone into 40 mL of toluene, and impregnating 100 g of the CC3 catalyst composition with the fluorenone containing solution. The impregnated catalyst was then allowed to sit open in a hood overnight to dry. The catalysts were reduced and utilized to hydrogenate an acetylene-containing gas mixture, as described in Example 1.

Figure 4:
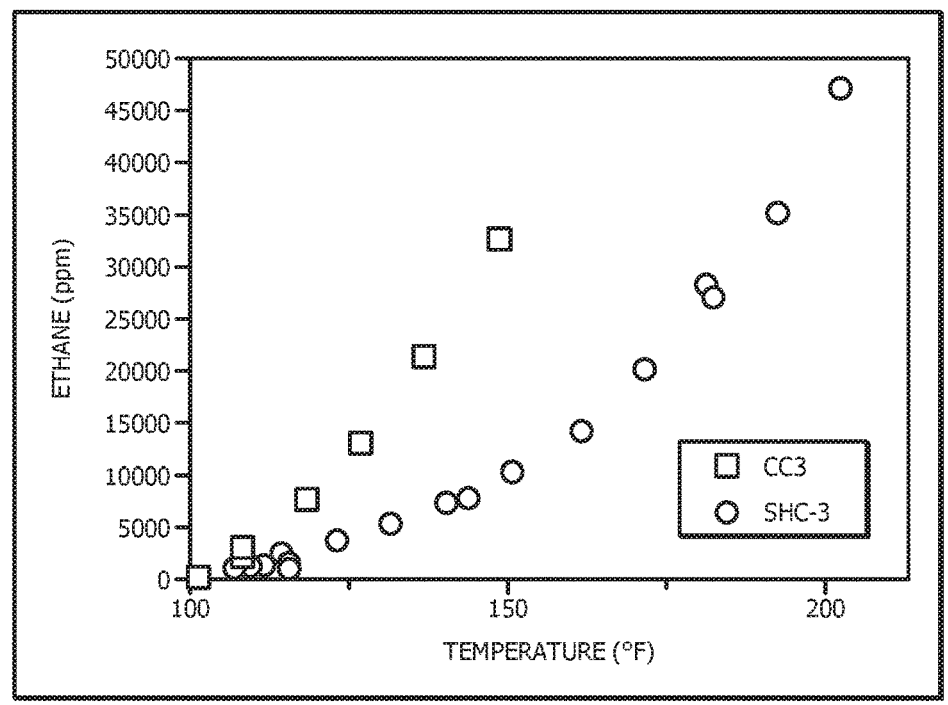
FIG. 4 is a plot of ethane make as a function of temperature for the catalysts of Example 3.

Results of this fluorenone containing catalyst along with the baseline CC3 catalyst are shown below in FIG. 4 and Table 3. FIG. 4 is a plot of ethane make (ppm) as a function of temperature (° F.) for the CC3 and SHC-3 catalysts. The fluorenone containing SHC-3 catalyst is superior to the comparative CC3 catalyst with respect to selectivity and operating window, having an operating window 98% greater than the comparative catalyst. Additionally, the starting activity of SHC-3 (as indicated by T1) is comparable to that of the CC3 catalyst as well.

TABLE 3

Pd/KF(3000 ppm) and Pd/KF(3000 ppm)/D Catalyst Performance from Example 3

|  | CC3 | SHC-3 |
|---|---|---|
| T1 (° F.) | 108 | 107 |
| T2 (° F.) | 151 | 192 |
| Operating Window (° F.) | 43 | 85 |

Example 4: Comparison of Dopants

To further study the effect of dopants according to this disclosure, a SHC catalyst, SHC-4, according to this disclosure comprising 1 weight percent fluorene as dopant was studied. A comparative catalyst, CC4, was prepared by impregnating 100 g of the CC1 catalyst composition of Example 1 with 40 mL of toluene, resulting in a catalyst comprising 400 ppm by weight (ppmw) palladium, 400 ppmw silver, and 1000 ppmw potassium.

SHC-4 was prepared as described hereinabove in Example 1 for SHC-1, with the use of fluorene in place of fluorenone. The SHC was reduced and utilized to hydrogenate an acetylene-containing gas mixture, as described in Example 1.

Figure 5:
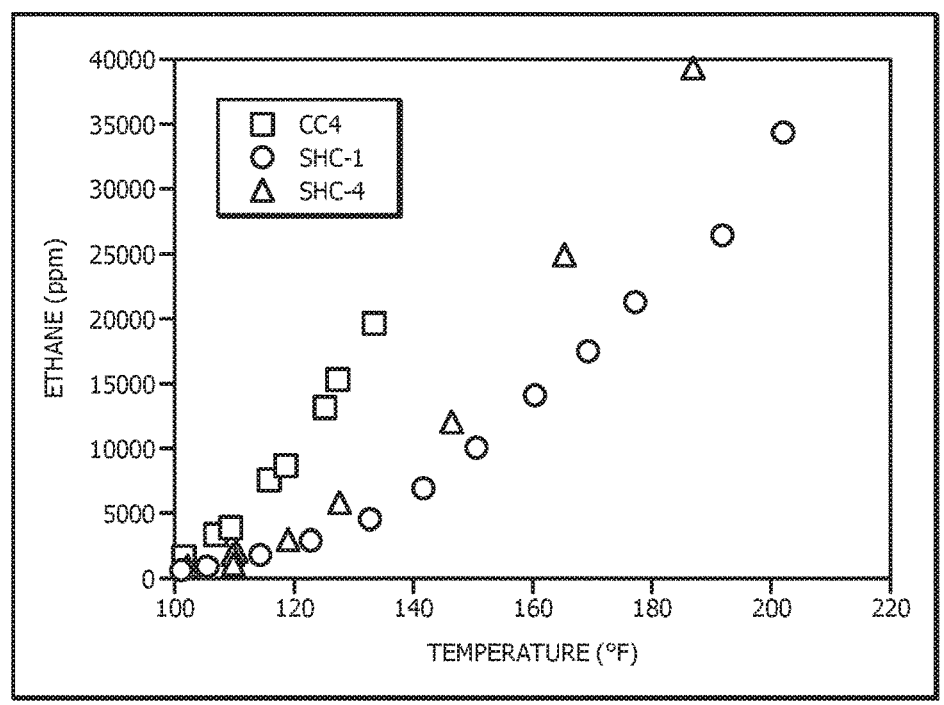
FIG. 5 is a plot of ethane make as a function of temperature for the catalysts of Example 4.

Results of this fluorene containing catalyst, SHC-4, along with the comparative CC4 catalyst, and the fluorenone containing SHC-1 of Example 1, are shown below in Table 4 and in FIG. 5. FIG. 5 is a plot of ethane make (ppm) as a function of temperature (° F.) for the CC4, SHC-4, and SHC-1 catalysts. The fluorene containing SHC-4 catalyst, and the fluorenone containing SHC-1 catalyst are superior to the comparative toluene-containing CC4 catalyst with respect to selectivity and operating window. SHC-4 has an operating window 44% greater than comparative catalyst CC4, while SHC-1 has an operating window 94% greater than comparative catalyst CC4. The starting activities (as indicated by T1) of SHC-4 and SHC-1 were comparable; CC4 had a slightly lower starting activity.

TABLE 4

Catalyst Performance from Example 4

|  | CC4 (Toluene) | SHC-4 (Fluorene) | SHC-1 (Fluorenone) |
|---|---|---|---|
| T1 (° F.) | 98 | 110 | 105 |
| T2 (° F.) | 148 | 182 | 202 |
| Operating Window (° F.) | 50 | 72 | 97 |

Example 5: Non-Fluorene Type Dopants

To further study the effect of dopants according to this disclosure, SHC catalysts, SHC-5, SHC-6, and SHC-7, according to this disclosure, comprising 1 weight percent chalcone, Michler's ketone, and 1,3-diphenyl-1,3-propanedione, respectively, as dopant were made as described above with reference to SHC-1, but with the specific dopants listed in place of the fluorenone of SHC-1. The SHC's were reduced and utilized to hydrogenate an acetylene-containing gas mixture, as described in Example 1.

Figure 6:
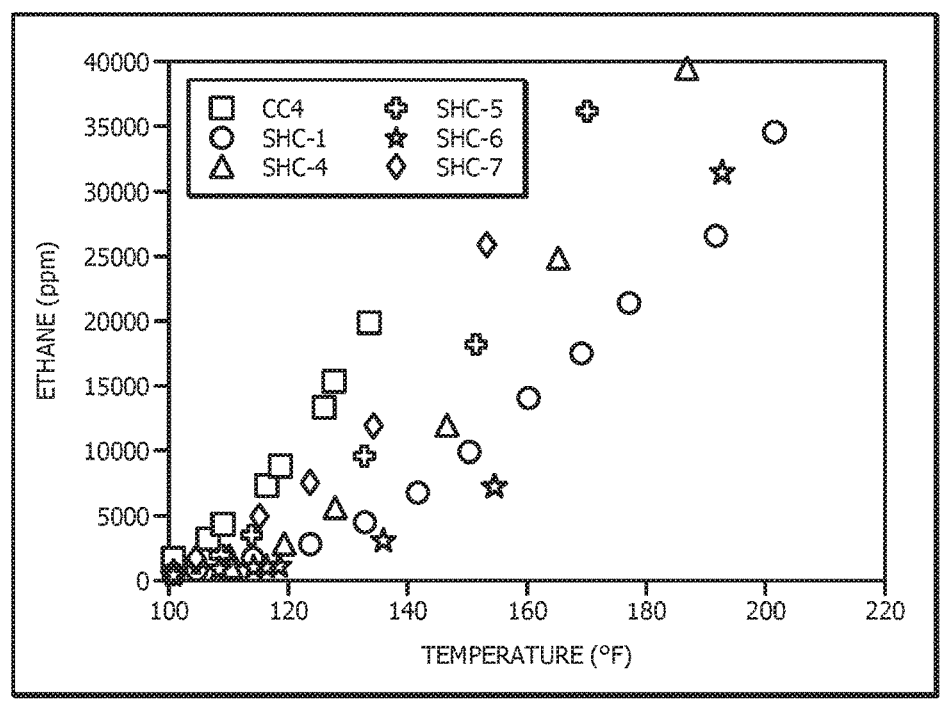
FIG. 6 is a plot of ethane make as a function of temperature for the catalysts of Example 5.

Results of these SHCs, along with the comparative CC4 catalyst, and the fluorenone containing SHC-1 catalyst of Example 1 and the fluorene-containing SHC-4 catalyst of Example 4, are shown below in Table 5 and in FIG. 6. FIG. 6 is a plot of ethane make (ppm) as a function of temperature (° F.) for the CC4, and SHC-1, SHC-4, SHC-5, SHC-6, and SHC-7 catalysts. The SHC's of this disclosure are superior to the comparative toluene-containing CC4 catalyst with respect to selectivity and operating window. Additionally, for some of these SHCs, the starting activities are comparable to baseline comparative catalyst CC4.

TABLE 5

Catalyst Performance from Example 5

|  | CC4 (Toluene) | SHC-1 (Fluorenone) | SHC-4 (Fluorene) | SHC-5 (Chalcone) | SHC-6 (Michler's Ketone) | SHC-7 (1,3-diphenyl-1,3-propanedione) |
|---|---|---|---|---|---|---|
| T1 (° F.) | 98 | 105 | 110 | 105 | 118 | 104 |
| T2 (° F.) | 148 | 202 | 182 | 169 | 197 | 162 |
| Operating Window (° F.) | 50 | 97 | 72 | 64 | 79 | 58 |

Additional Embodiments

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

The following are nonlimiting, specific embodiments in accordance with the present disclosure:

A: A composition comprising: a supported hydrogenation catalyst comprising palladium and a support, wherein the supported hydrogenation catalyst is capable of selectively hydrogenating highly unsaturated hydrocarbons to unsaturated hydrocarbons; and a dopant, wherein the dopant comprises a fluorene structure.

B: A method of making a selective hydrogenation catalyst, the method comprising: contacting a support with a palladium-containing compound to form a supported-palladium composition; contacting the supported-palladium composition with a dopant to form a selective hydrogenation catalyst precursor, wherein the dopant comprises a fluorene structure; and reducing the selective hydrogenation catalyst precursor to form the selective hydrogenation catalyst.

C: A selective hydrogenation catalyst prepared by contacting a support with a palladium-containing compound to form a supported-palladium composition; contacting the supported-palladium composition with a dopant to form a selective hydrogenation catalyst precursor, wherein the dopant comprises a fluorene structure; and reducing the selective hydrogenation catalyst precursor to form the selective hydrogenation catalyst.

D: A method of selectively hydrogenating highly unsaturated hydrocarbons to an unsaturated hydrocarbon enriched composition, the method comprising: contacting a supported catalyst comprising palladium and a dopant with a feed comprising highly unsaturated hydrocarbon under conditions suitable for hydrogenating at least a portion of the highly unsaturated hydrocarbon feed to form the unsaturated hydrocarbon enriched composition, wherein the dopant comprises a fluorene structure.

Each of embodiments A, B, C, and D may have one or more of the following additional elements: Element 1: wherein the dopant further comprises a substituent selected from carboxyl groups, hydroxyl groups, carbonyl groups, amide groups, phenyl groups, substituted phenyl groups, or combinations thereof. Element 2: wherein the at least one substituent is located on the 1, 2, 4, or 9 position of the fluorene structure. Element 3: wherein the dopant is 9-phenyl-9-fluorenol, 9-hydroxyfluorene, 2-hydroxyfluorene, 9-(2-(hydroxymethyl)phenyl)-9-fluorenol, fluorene-9-carboxylic acid, fluorene-1-carboxylic acid, fluorene-4-carboxylic acid, fluorenone, fluorene, or a combination thereof. Element 4: wherein the dopant has a boiling point of greater than or equal to about 200° C. Element 5: further comprising at least one component selected from Group 1B metals, Group 1B metal compounds, silver, silver compounds, fluorine, fluoride compounds, sulfur, sulfur compounds, alkali metal, alkali metal compounds, alkaline metals, alkaline metal compounds, iodine, iodide compounds, or combinations thereof disposed on the support. Element 6: comprising an inorganic support. Element 7: wherein the palladium is present in an amount of from about 0.005 wt. % to about 5 wt. % based on the total weight of the catalyst. Element 8: wherein the dopant is present in an amount of from about 0.005 wt. % to about 5 wt. % based on the total weight of the catalyst. Element 9: wherein the support has a surface area of from about 2 m$^2$/g to about 100 m$^2$/g, and wherein greater than about 90 wt. % of the palladium is concentrated near a periphery of the support. Element 10: wherein the support, the supported-palladium composition, the selective hydrogenation catalyst precursor, or the selective hydrogenation catalyst further comprises at least one component selected from Group 1B metals, Group 1B metal compounds, silver, silver compounds, fluorine, fluoride compounds, sulfur, sulfur compounds, alkali metal, alkali metal compounds, alkaline metals, alkaline metal compounds, iodine, iodide compounds, or combinations thereof. Element 11: further comprising contacting the support, the supported-palladium composition, or the selective hydrogenation catalyst precursor with at least one selectivity enhancer. Element 12: wherein the at least one selectivity enhancer is selected from Group 1B metals, Group 1B metal compounds, silver, silver compounds, fluorine, fluoride compounds, sulfur, sulfur compounds, alkali metal, alkali metal compounds, alkaline metals, alkaline metal compounds, iodine, iodide compounds, or combinations thereof. Element 13: wherein the selectivity enhancer comprises elemental silver, silver nitrate, silver acetate, silver bromide, silver chloride, silver iodide, silver fluoride, or combinations thereof. Element 14: wherein the selectivity enhancer comprises elemental alkali metal, alkali metal fluoride, alkali metal chloride, alkali metal bromide, alkali metal iodide, alkali metal oxide, alkali metal carbonate, alkali metal sulfate, alkali metal phosphate, alkali metal borate, potassium fluoride, or combinations thereof. Element 15: wherein the selectivity enhancer comprises silver and potassium fluoride. Element 16: wherein the selectivity enhancer is present in an amount of from about 0.005 wt. % to about 5 wt. % based on the total weight of the selective hydrogenation catalyst. Element 17: wherein the selectivity enhancer is present in an amount of from about 0.01 wt. % to about 5 wt. % based on the total weight of the selective hydrogenation catalyst. Element 18: further comprising drying the catalyst precursor at a temperature in the range of from about 0° C. to about 150° C. for a time period in the range of from about 0.1 hour to about 100 hours. Element 19: wherein the support comprises at least one component selected from aluminas, silicas, titanias, zirconias, aluminosilicates, spinels, or combinations thereof. Element 20: wherein the highly unsaturated hydrocarbons comprise at least one component selected from acetylene, methylacetylene, propadiene, butadiene, or combinations thereof. Element 21: wherein the conditions suitable for hydrogenation include conducting the step of contacting at a temperature less than about the boiling point of the dopant. Element 22: further comprising increasing the temperature to a temperature greater than or equal to about the boiling point of the dopant.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference, to the extent that they provide exemplary, procedural or other details supplementary to those set forth herein.

What is claimed is:

1. A composition comprising:
   a supported hydrogenation catalyst comprising palladium and an inorganic support selected from the group consisting of aluminas, silicas, titanias, zirconias, aluminosilicates, spinels, and combinations thereof, wherein the supported hydrogenation catalyst is capable of selectively hydrogenating highly unsaturated hydrocarbons to unsaturated hydrocarbons; and
   a dopant, wherein the dopant comprises a fluorene structure

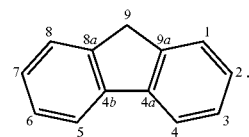

2. The composition of claim 1, wherein the dopant further comprises at least one substituent selected from the group consisting of carboxyl groups, hydroxyl groups, carbonyl groups, amide groups, phenyl groups, substituted phenyl groups, and combinations thereof.

3. The composition of claim 2, wherein the at least one substituent is located on the 1, 2, 4, or 9 position of the fluorene structure.

4. The composition of claim 3, wherein the dopant comprises 9-phenyl-9-fluorenol, 9-hydroxyfluorene, 2-hydroxyfluorene, 9-(2-(hydroxymethyl)phenyl)-9-fluorenol, fluorene-9-carboxylic acid, fluorene-1-carboxylic acid, fluorene-4-carboxylic acid, fluorenone, fluorene, or a combination thereof.

5. The composition of claim 1, wherein the dopant has a boiling point of greater than or equal to about 200° C.

6. The composition of claim 1 further comprising at least one selectivity enhancer selected from the group consisting of Group 1B metals, Group 1B metal compounds, silver, silver compounds, fluorine, fluoride compounds, sulfur, sulfur compounds, alkali metal, alkali metal compounds, alkaline metals, alkaline metal compounds, iodine, iodide compounds, and combinations thereof, disposed on the inorganic support.

7. The composition of claim 1, wherein the palladium is present in an amount of from about 0.005 wt. % to about 5 wt. % based on the total weight of the catalyst.

8. The composition of claim 1, wherein the dopant is present in an amount of from about 0.005 wt. % to about 5 wt. % based on the total weight of the catalyst.

9. The composition of claim 1, wherein the inorganic support has a surface area of from about 2 m²/g to about 100 m²/g, and wherein greater than about 90 wt. % of the palladium is concentrated near a periphery of the inorganic support.

10. A method of making a selective hydrogenation catalyst, the method comprising:
    contacting an inorganic support selected from the group consisting of aluminas, silicas, titanias, zirconias, aluminosilicates, spinels, and combinations thereof with a palladium-containing compound to form a supported-palladium composition;
    contacting the supported-palladium composition with a dopant to form a selective hydrogenation catalyst precursor, wherein the dopant comprises a fluorene structure

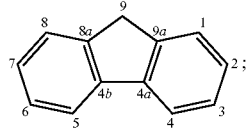

and
reducing the selective hydrogenation catalyst precursor to form the selective hydrogenation catalyst.

11. The method of claim 10, wherein the dopant further comprises at least one substituent selected from the group consisting of carboxyl groups, hydroxyl groups, carbonyl groups, amide groups, phenyl groups, substituted phenyl groups, and combinations thereof.

12. The method of claim 11, wherein the at least one substituent is located on the 1, 2, 4, or 9 position of the fluorene structure.

13. The method of claim 12, wherein the dopant comprises 9-phenyl-9-fluorenol, 9-hydroxyfluorene, 2-hydroxyfluorene, 9-(2-(hydroxymethyl)phenyl)-9-fluorenol, fluorene-9-carboxylic acid, fluorene-1-carboxylic acid, fluorene-4-carboxylic acid, fluorenone, fluorene, or a combination thereof.

14. The method of claim 10, wherein the dopant has a boiling point of greater than or equal to about 200° C.

15. The method of claim 10 further comprising contacting the inorganic support, the supported-palladium composition, the selective hydrogenation catalyst precursor, or the selective hydrogenation catalyst with at least one selectivity enhancer selected from the group consisting of Group 1B metals, Group 1B metal compounds, silver, silver compounds, fluorine, fluoride compounds, sulfur, sulfur compounds, alkali metal, alkali metal compounds, alkaline metals, alkaline metal compounds, iodine, iodide compounds, and combinations thereof.

16. The method of claim 15, wherein the selectivity enhancer comprises elemental silver, silver nitrate, silver acetate, silver bromide, silver chloride, silver iodide, silver fluoride, or combinations thereof.

17. The method of claim 15, wherein the selectivity enhancer comprises elemental alkali metal, alkali metal fluoride, alkali metal chloride, alkali metal bromide, alkali metal iodide, alkali metal oxide, alkali metal carbonate, alkali metal sulfate, alkali metal phosphate, alkali metal borate, potassium fluoride, or combinations thereof.

18. The method of claim 17, wherein the selectivity enhancer is present in an amount of from about 0.01 wt. % to about 5 wt. % based on the total weight of the selective hydrogenation catalyst.

19. The method of claim 15, wherein the selectivity enhancer comprises silver and potassium fluoride.

20. The method of claim 15, wherein contacting the inorganic support, the supported-palladium composition, the selective hydrogenation catalyst precursor, or the selective hydrogenation catalyst with the least one selectivity enhancer comprises incipient wetness impregnation.

21. The method of claim 10, wherein the palladium is present in an amount of from about 0.005 wt. % to about 5 wt. % Pd based on the total weight of the selective hydrogenation catalyst.

22. The method of claim 10, wherein the dopant is present in an amount of from about 0.005 wt. % to about 5 wt. % based on the total weight of the selective hydrogenation catalyst.

23. A selective hydrogenation catalyst prepared according the method of claim 10.

24. The method of claim 10, wherein contacting the inorganic support with the palladium-containing compound to form the supported-palladium composition and contacting the supported-palladium composition with the dopant to form the selective hydrogenation catalyst precursor comprise incipient wetness impregnation.

25. A method of selectively hydrogenating highly unsaturated hydrocarbons to an unsaturated hydrocarbon enriched composition, the method comprising:
contacting a supported catalyst comprising palladium and a dopant with a feed comprising highly unsaturated hydrocarbon under conditions suitable for hydrogenating at least a portion of the highly unsaturated hydrocarbon feed to form the unsaturated hydrocarbon enriched composition, wherein the dopant comprises a fluorine structure

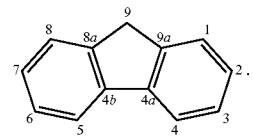

26. The method of claim 25, wherein the highly unsaturated hydrocarbons comprise acetylene, methylacetylene, propadiene, butadiene, or a combination thereof.

27. The method of claim 25, wherein the conditions suitable for hydrogenation include conducting the step of contacting at a temperature less than about the boiling point of the dopant.

28. The method of claim 27 further comprising increasing the temperature to a temperature greater than or equal to about the boiling point of the dopant.

* * * * *